United States Patent [19]

Bernardon

[11] Patent Number: 5,763,487

[45] Date of Patent: Jun. 9, 1998

[54] BIOACTIVE BICYCLIC AROMATIC COMPOUNDS AND PHARMACEUTICAL/COSMETIC COMPOSITIONS COMPRISED THEREOF

[75] Inventor: Jean-Michel Bernardon, Le Rouret, France

[73] Assignee: Centre International de Recherches Dermatologiques Galderma, Valbonne, France

[21] Appl. No.: 589,388

[22] Filed: Jan. 22, 1996

[30] Foreign Application Priority Data

Jan. 20, 1995 [FR] France .................................. 95-00659

[51] Int. Cl.⁶ .............................. A61K 31/19; C07C 57/38
[52] U.S. Cl. .......................... 514/569; 560/10; 562/427; 562/467; 514/844; 514/861; 514/863; 514/864; 514/887; 514/912
[58] Field of Search ............................... 560/10; 562/427, 562/467; 514/569, 544

[56] References Cited

U.S. PATENT DOCUMENTS 5,248,823  9/1993  Janssen et al.

*Primary Examiner*—Robert W. Ramsuer
*Attorney, Agent, or Firm*—Burns, Doane, Swecker & Mathis, L.L.P.

[57] ABSTRACT

Novel pharmaceutically/cosmetically-active bicyclic aromatic compounds have the structural formula (I):

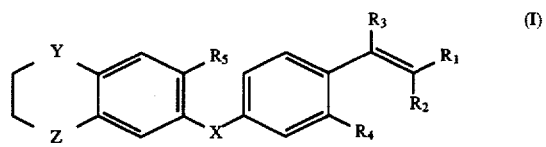

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

25 Claims, 2 Drawing Sheets

BIOACTIVE BICYCLIC AROMATIC COMPOUNDS AND PHARMACEUTICAL/COSMETIC COMPOSITIONS COMPRISED THEREOF

BACKGROUND OF THE INVENTION

Technical Field of the Invention

The present invention relates to novel bicyclic aromatic compounds and to pharmaceutical/cosmetic compositions comprised thereof; the subject compounds are especially useful in human or veterinary medicine, or alternatively in cosmetic compositions.

SUMMARY OF THE INVENTION

The compounds according to the invention display marked activity in the fields of cell differentiation and cell proliferation, and are particularly useful in the topical and systemic treatment of dermatological conditions associated with a keratinization disorder, dermatological (and other) conditions including an inflammatory and/or immunoallergic component, and dermal or epidermal proliferations, whether benign or malignant. The subject compounds can, in addition, be used for the treatment of degenerative diseases of the connective tissue, for combating skin aging, whether photoinduced or chronological, and for treating cicatrization disorders. They are also useful for ophthalmological applications, especially for the treatment of corneopathies.

The compounds according to the invention can also be formulated into cosmetic compositions for body and hair hygiene.

Briefly, the bicyclic aromatic compounds according to this invention have the following structural formula (I):

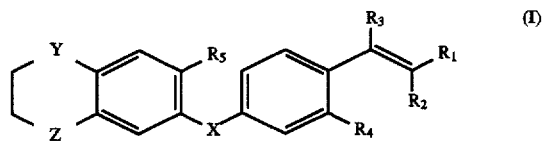

in which $R_1$ is (i) a hydrogen atom, (ii) the —$CH_3$ radical, (iii) a radical —$CH_2OR_6$, (iv) a radical —O—$R_8$ only in the event that $R_2$ and $R_4$ together form, with the benzene ring adjacent thereto, a naphthalene ring member, (v) a radical —CO—$R_{10}$, (vi) a radical —$S(O)_p$—$R_{12}$, in which $R_6$, $R_8$, $R_{10}$, $R_{12}$ and p are as defined below; $R_2$ and $R_3$ are, whether independently or taken together, and in the event that they are independent, $R_2$ is a hydrogen atom, a lower alkyl radical, a hydroxyl radical, a radical —$OR_7$, a radical —O—$COR_7$, an amino radical or a radical —NH—$COR_7$ and $R_3$ is a hydrogen atom or a lower alkyl radical, and in the event that they are taken together, $R_2$ and $R_3$ together form, with the ethylenic double bond bridging same, an acetylenic triple bond; $R_2$ and $R_4$ are, whether independently or taken together, and in the event that they are independent, $R_2$ is as defined above and $R_4$ is a hydrogen atom, a linear or branched alkyl radical having from 1 to 20 carbon atoms, a hydroxyl radical, a radical —$OR_7$ or a radical —O—$COR_7$, and in the event that they are taken together, $R_2$ and $R_4$ together form, with the benzene ring from which they depend, a naphthalene ring member, in which $R_7$ is as defined below; $R_5$ is a hydrogen atom, a halogen atom, a lower alkyl radical, an $NO_2$ radical, a hydroxyl radical, a radical —$OR_7$, a radical —O—$COR_7$, or a radical:

in which $R_7$, $R_{13}$ and $R_{14}$ are as defined below; X is —O—, —$S(O)_t$— or —$NR_{12}$—, wherein t and $R_{12}$ are as defined below; Y and Z, which may be identical or different, are each —$CR_{13}R_{14}$—, —O— or —$S(O)_t$—, with the proviso that Y and Z cannot simultaneously be an oxygen atom and cannot simultaneously be a radical —$S(O)_t$—, wherein t, $R_{13}$ and $R_{14}$ are as defined below; $R_6$ is a hydrogen atom, a lower alkyl radical, or a radical —$COR_7$; $R_7$ is a lower alkyl radical; $R_8$ is a hydrogen atom, a lower alkyl radical, or a radical —$(CH_2)_m$—$(CO)_n$—$R_9$, wherein $R_9$ is a lower alkyl radical or a heterocycle; $R_{10}$ is (a) a hydrogen atom, (b) a lower alkyl radical, (c) a radical:

or (d) a radical —O—$R_{11}$, wherein $R_{11}$ is a hydrogen atom, a linear or branched alkyl radical having from 1 to 20 carbon atoms, an alkenyl radical, a mono- or polyhydroxyalkyl radical, an optionally substituted aryl or aralkyl radical, a sugar radical, or an aminoacid residue or peptide residue; $R_{12}$ is a hydrogen atom, or a lower alkyl radical; $R_{13}$ and $R_{14}$ are each a hydrogen atom, or a lower alkyl radical; m is an integer ranging from 1 to 3; n is 0 or 1; p is an integer ranging from 0 to 3; t is 0, 1 or 2; and R' and R" are each, independently, a hydrogen atom, a lower alkyl radical, a mono- or polyhydroxyalkyl radical, an optionally substituted aryl radical or an aminoacid residue or sugar radical, with the proviso that R' and R" may together form a heterocycle.

This invention also features the salts of the compounds of formula (I) in the event that $R_1$ represents a carboxylic acid function, a sulfonic acid function, or in the event that the radical $R_5$ represents an amine function. It also relates to the optical and geometrical isomers of said compounds.

When the compounds according to the invention are in the form of salts, these are preferably salts of an alkali or alkaline earth metal, or salts of zinc or of an organic amine.

BRIEF DESCRIPTION OF THE DRAWINGS

The FIGURES OF DRAWING set forth reaction schemes/mechanisms illustrating syntheses for the preparation of the bicyclic aromatic compounds according to the present invention.

DETAILED DESCRIPTION OF BEST MODE AND SPECIFIC/PREFERRED EMBODIMENTS OF THE INVENTION

Figure 1:
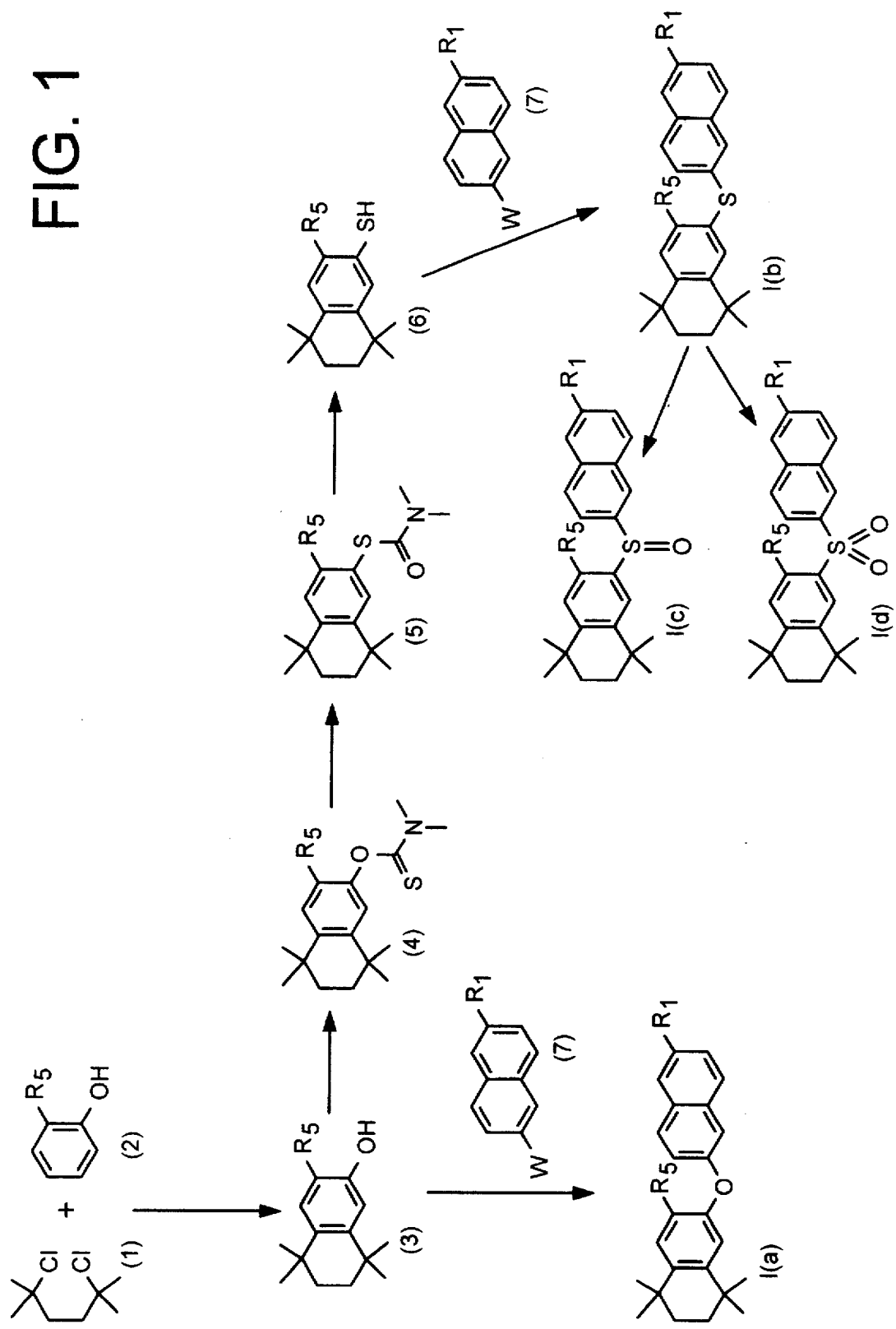

More particularly according to the present invention, by the term "lower alkyl radical" is intended an alkyl radical having from 1 to 12, preferably from 1 to 9, carbon atoms, advantageously methyl, ethyl, isopropyl, butyl, tert-butyl, hexyl, nonyl and dodecyl radicals.

By the term "linear or branched alkyl radical having from 1 to 20 carbon atoms" is preferably intended methyl, ethyl, propyl, 2-ethylhexyl, octyl, dodecyl, hexadecyl and octadecyl radicals.

By the term "monohydroxyalkyl" radical is intended a radical preferably having 2 or 3 carbon atoms, in particular a 2-hydroxyethyl, 2-hydroxypropyl or 3-hydroxypropyl radical.

By the term "polyhydroxyalkyl radical" is intended a radical preferably having from 3 to 6 carbon atoms and 2 to 5 hydroxyl groups, such as 2,3-dihydroxypropyl, 2,3,4-trihydroxybutyl, 2,3,4,5-tetrahydroxypentyl radicals, or a pentaerythritol residue.

By the term "aryl radical" is preferably intended a phenyl radical optionally substituted by at least one halogen atom, or a hydroxyl or nitro functional group.

By the term "aralkyl radical" is preferably intended a benzyl or phenethyl radical optionally substituted by at least one halogen atom, or a hydroxyl or nitro functional group.

By the term "alkenyl radical" is intended a radical preferably having from 2 to 5 carbon atoms and one or more sites of ethylenic unsaturation, such as, more particularly, the allyl radical.

By the term "sugar radical" is intended a radical derived, in particular, from glucose, galactose or mannose, or from glucuronic acid.

By the term "aminoacid residue" is especially intended a residue derived from lysine, glycine or aspartic acid, and by the term "peptide residue" is more particularly intended a dipeptide or tripeptide residue prepared via the combination of amino acids.

Lastly, by the term "heterocycle" is preferably intended a piperidino, morpholino, pyrrolidino or piperazino radical, optionally substituted at the 4-position by a $C_1$–$C_6$ alkyl radical or mono- or polyhydroxyalkyl radical as defined above.

Among the halogen atoms, preferred are the fluorine, chlorine and bromine atoms.

Among the compounds of formula (I) according to the present invention, particularly representative are the following:

6-(5,6,7,8-Tetrahydro-5,5,8,8-tetramethyl-2-naphthyloxy)naphthoic acid;

4-(5,6,7,8-Tetrahydro-5,5,8,8-tetramethyl-2-naphthyloxy)cinnamic acid;

β-Methyl-4-(5,6,7,8-tetrahydro-5,5,8,8-tetramethyl-2-naphthyloxy)cinnamic acid;

4-(5,6,7,8-Tetrahydro-5,5,8,8-tetramethyl-2-naphthyloxy)phenylpropiolic acid;

6-(3,5,5,8,8-Pentamethyl-5,6,7,8-tetrahydro-2-naphthyloxy)naphthoic acid;

6-(5,6,7,8-Tetrahydro-5,5,8,8-tetramethyl-2-naphthylthio)naphthoic acid;

6-(5,6,7,8-Tetrahydro-5,5,8,8-tetramethyl-2-naphthylsulfinyl)naphthoic acid;

6-(5,6,7,8-Tetrahydro-5,5,8,8-tetramethyl-2-naphthylsulfonyl)naphthoic acid;

6-(5,6,7,8-Tetrahydro-5,5,8,8-tetramethyl-2-naphthylamino)naphthoic acid;

α-Hydroxy-4-(5,6,7,8-tetrahydro-5,5,8,8-tetramethyl-2-naphthyloxy)cinnamic acid;

α-Acetamido-4-(5,6,7,8-tetrahydro-5,5,8,8-tetramethyl-2-naphthyloxy)cinnamic acid 6-(3,5,5,8,8-Pentamethyl-5,6,7,8-tetrahydro-2-naphthylthio)naphthoic acid;

6-(3,5,5,8,8-Pentamethyl-5,6,7,8-tetrahydro-2-naphthylsulfonyl)naphthoic acid;

6-(3-Bromo-5,6,7,8-tetrahydro-5,5,8,8-tetramethyl-2-naphthyloxy)naphthoic acid;

6-(5,6,7,8-Tetrahydro-5,5,8,8-tetramethyl-2-naphthyloxy)naphthalenemethanol;

N-Ethyl-6-(5,6,7,8-tetrahydro-5,5,8,8-tetramethyl-2-naphthyloxy)naphthalenecarboxamide;

6-(5,6,7,8-Tetrahydro-5,5,8,8-tetramethyl-2-naphthyloxy)naphthalenecarboxamide;

6-(5,6,7,8-Tetrahydro-5,5,8,8-tetramethyl-2-naphthyloxy)naphthoic acid morpholide;

6-(5,6,7,8-Tetrahydro-5,5,8,8-tetramethyl-2-naphthyloxy)naphthalenecarbaldehyde.

According to the present invention, the preferred compounds of formula (I) are those in which at least one of the conditions below are satisfied:

$R_1$ is a radical —CO—$R_{10}$;

X represents —O—, —S—, or —$NR_{12}$—;

$R_2$ represents a hydrogen atom or a lower alkyl radical;

$R_2$ and $R_4$ together form, with the benzene ring from which they depend, a naphthalene ring system;

$R_2$ and $R_3$ together form, with the ethylenic double bond bridging same, an acetylenic triplebond.

Figure 2:
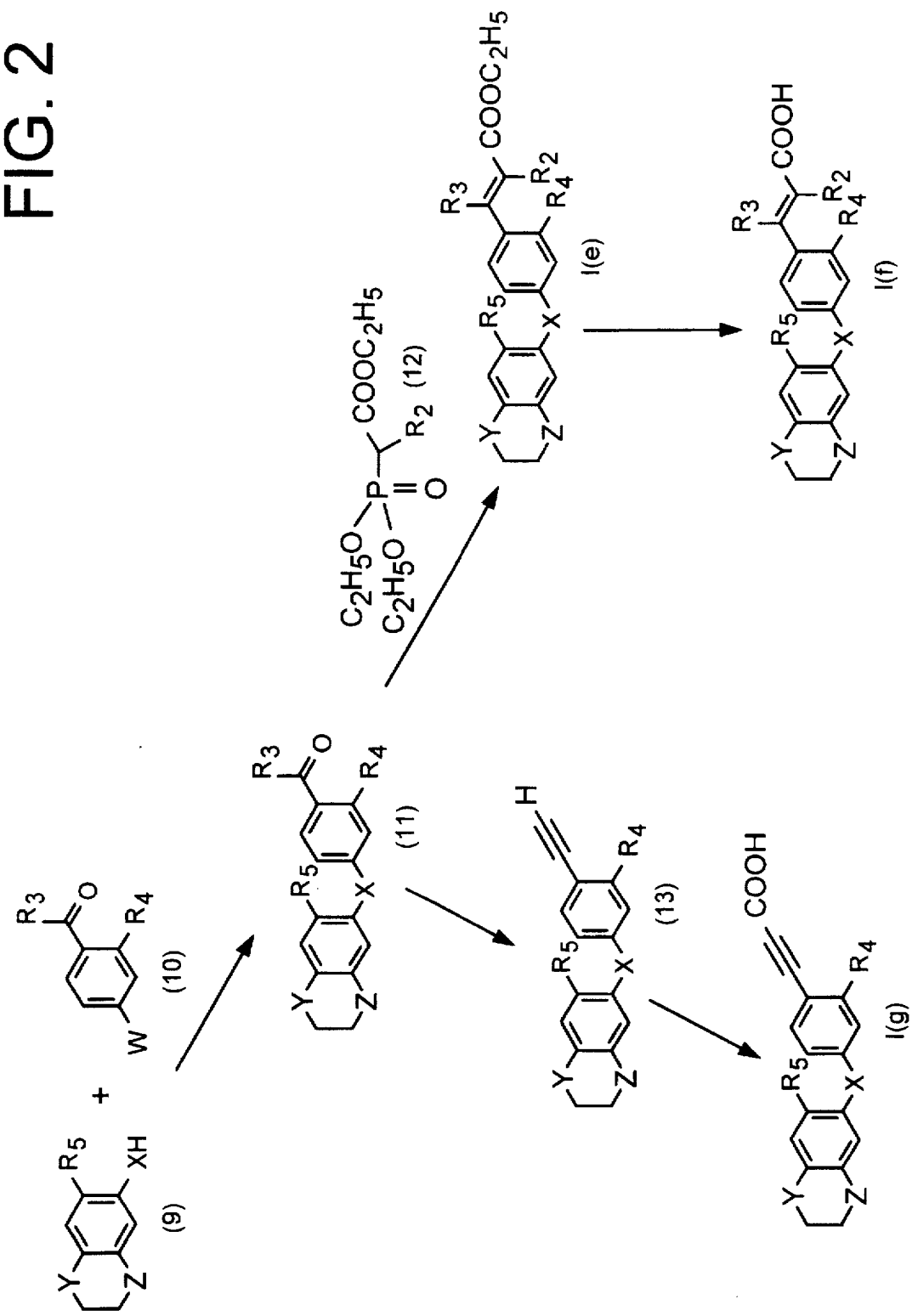

The present invention also features the processes for the preparation of the compounds of formula (I), in particular via the reaction schemes illustrated in the FIGS. 1 and 2 of the Drawings.

Thus, the compounds of formula I (a) can be prepared (FIG. 1) from the sodium salt of the phenol derivative (3) by coupling with a halogenated derivative (7), preferably a bromo or iodo compound, in the presence of a complex of copper bromide and dimethyl sulfide, in a solvent such as pyridine. The phenol derivatives (3) can be prepared via Friedel-Crafts reaction from a phenol (2) and a dihalogenated compound (1) in the presence of a Lewis acid, for example aluminum chloride.

The compounds of formula I (b) can be prepared (FIG. 1) from the sodium salt of the thiol derivative (6) by coupling with a halogenated derivative (7), preferably a bromo or iodo compound, in the presence of a catalyst such as certain transition metal complexes, in an alcoholic solvent such as ethyl or butyl alcohol.

Exemplary catalysts include those derived from nickel or palladium, for example the complexes of $Ni^{II}$ with various phosphines, and tetrakis(triphenylphosphine)palladium(0).

The thiol compounds (6) can be prepared from phenol derivatives (3) via the dialkylthiocarbamate derivatives (4) and (5) in accordance with the general conditions described by M. Newman and H. Karnes in *J. Org. Chem.*, 31, 3980–4 (1966).

The compounds of formulae I (c) and I (d) can subsequently be prepared by oxidation of the derivative I (b), for example by employing meta-chloroperbenzoic acid.

The compounds of formula I (g) can be prepared (FIG. 2) from the acetylene derivative (13) by reaction with n-butyllithium followed by carboxylation in the presence of $C_2$. The acetylene compounds (13) can be prepared:

(a) from aldehyde derivatives (11) (when $R_3$ is a hydrogen atom), by reaction with carbon tetrabromide and triphenylphosphine to provide a 2',2'-dibromostyrene compound which is converted into the acetylene derivative by means of a non-nucleophilic base, such as n-butyllithium, in an aprotic solvent such as tetrahydrofuran;

(b) from ketone derivatives (11) (when R3 is a lower alkyl), by a sequence of reactions comprising treatment with a base, such as lithium diisopropylamide, then with a dialkyl phosphate chloride and again with lithium diisopropylamide.

The compounds of formula I (e) can be prepared (FIG. 2) from aldehyde or ketone derivatives (11) according to a Horner reaction with a lithium compound derived from a phosphonate (12). Subsequently, by hydrolysis in alcoholic potassium hydroxide or sodium hydroxide solution, the compounds of formula I (f) are obtained.

When in the general formula (I) X represents —$NR_{12}$, the compounds I (h) can be prepared in accordance with an Ullman reaction by direct nucleophilic displacement of a halogenated derivative (7), preferably an iodo compound, by an aniline derivative (8) in the presence of a base, such as potassium carbonate or N-methylmorpholine, and copper.

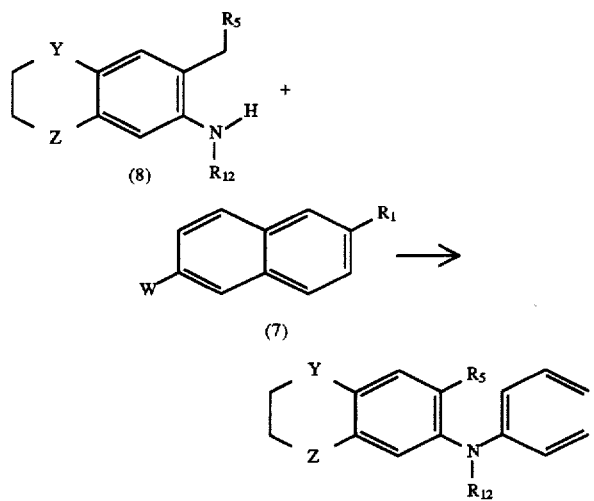

In the formulae and reactions described above, and in the Figures of Drawing, W represents a halogen atom.

Also, in the formulae and reactions described above; and in the Figures of Drawings, $R_1$, $R_2$, $R_3$, $R_4$, $R_5$, X, Y and Z have the same definitions as those given above in respect of the general formula (I) or are derivatives thereof which are suitably protected in order to be compatible with the conditions of reaction. In particular, when $R_1$, $R_2$, $R_4$ and $R_5$ represent the hydroxyl radical, the latter is preferably protected in the tert-butyldimethylsilyloxy or methoxyethoxymethoxy form. Deprotection is carried out either in the presence of tetrabutylammonium fluoride, trimethylsilane iodide or in an acidic medium (for example hydrochloric acid).

The present invention also features therapeutic/pharmaceutical applications of the compounds of formula (I).

These compounds exhibit activity in the mouse embryonal teratocarcinoma (F9) cell differentiation test (Cancer Research, 43, p. 5268 (1983)) and/or in the test for inhibition of ornithine decarboxylase after induction by TPA in the mouse (Cancer Research, 38, pp. 793–801 (1978)). These tests demonstrate the activities of the subject compounds in the fields, respectively, of cell differentiation and cell proliferation.

The compounds according to the invention are particularly suitable in the following fields of therapy:

(1) For treating dermatological conditions associated with a keratinization disorder related to differentiation and proliferation, especially for treating acne vulgaris or comedo, polymorphic or rosacea acnes, nodulocystic acne or acne conglobata, senile acnes, secondary acnes such as solar acne, acne medicamentosa or occupational acne;

(2) For treating other types of keratinization disorders, especially ichthyoses, ichthyosiform states, Darier's disease, palmoplantar keratodermias, leucoplakias and leucoplakia-like states, skin or mucous (buccal) lichen;

(3) For treating other dermatological conditions associated with a keratinization disorder manifesting an inflammatory and/or immunoallergic component, and, in particular, all forms of psoriasis, whether cutaneous, mucous or ungual, and also psoriatic rheumatism, or skin atopy, such as eczema or respiratory atopy or gingival hypertrophy; the compounds can also be used for treating certain inflammatory conditions which do not exhibit any keratinization disorder;

(4) For treating all dermal or epidermal proliferations, whether benign or malignant, and whether or not of viral origin, such as verruca vulgaris, verruca plana and verruciform epidermodyplasia, oral or florid papillomatoses and proliferations which can be induced by ultraviolet radiation, especially in the case of basocellular and spinocellular epitheliomas;

(5) For treating other dermatological disorders, such as bullous dermatoses and collagen diseases;

(6) For treating certain ophthalmological disorders, especially corneopathies;

(7) For repairing or combating skin aging, whether photoinduced or chronological, or for reducing pigmentations and actinic keratoses, or any pathologies associated with chronological or actinic aging;

(8) For preventing or curing the stigmas of epidermal and/or dermal atrophy induced by local or systemic corticosteroids, or any other form of skin atrophy;

(9) For preventing or treating cicatrization disorders or for preventing or repairing vibices;

(10) For combating disorders of the sebaceous function, such as acne hyperseborrhoea or simple seborrhoea;

(11) For the treatment or prevention of cancerous or precancerous states;

(12) For the treatment of inflammatory conditions such as arthritis;

(13) For the treatment of any condition of viral origin, at the level of the skin or in general;

(14) For the prevention or treatment of alopecia;

(15) For the treatment of dermatological or general conditions which have an immunological component;

(16) For the treatment of conditions of the cardiovascular system, such as arteriosclerosis.

For the aforesaid therapeutic or pharmaceutical applications, the compounds according to the invention can advantageously be used in combination with other compounds displaying retinoid-type activity, with the D vitamins or derivatives thereof, with corticosteroids, with free-radical scavengers, with α-hydroxy or α-keto acids or derivatives thereof, or with ion channel blockers. By the term "D vitamins or derivatives thereof" are intended, for example, the derivatives of vitamin $D_2$ or $D_3$ and, in particular, 1,25-dihydroxyvitamin $D_3$. By the term "free-radical scavengers" are intended, for example, α-tocopherol, superoxide dismutase, ubiquinol or certain metalchelating agents. By the term "α-hydroxy or α-keto acids or derivatives thereof" are intended, for example, lactic, malic, citric, glycolic, mandelic, tartaric, glyceric or ascorbic acid or salts, amides or esters thereof. Lastly, by the term "ion channel blockers" are intended, for example, minoxidil (2,4-diamino-6-piperidino-pyrimidine 3-oxide) and derivatives thereof.

The present invention thus also features medicinal compositions comprising at least one compound of formula (I) as defined above, one of its optical or geometric isomers, or one of its pharmaceutically acceptable salts or other derivatives thereof.

The pharmaceutical/therapeutic compositions of this invention, intended, in particular, for the treatment of the aforesaid disease states, comprise a carrier, vehicle or diluent which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out enterally, parenterally, topically or ocularly.

For enteral administration, the medicinal/pharmaceutical compositions may be in the form of tablets, gelatin capsules, coated tablets, syrups, suspensions, solutions, elixirs, powders, granules, emulsions, microspheres or nanospheres or lipid or polymeric vesicles which permit controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for treatment of the skin and mucosae and can therefore be provided in the form of ointments, creams, milks, salves, powders, impregnated pads, solutions, gels, sprays, lotions or suspensions. They may also be provided in the form of microspheres or nanospheres or lipid or polymer vesicles or polymeric patches and hydrogels which permit a controlled release. These compositions for topical administration can, moreover, be provided either in anhydrous form or in an aqueous form, depending on the particular clinical indication.

For ocular administration, the compositions are principally collyria.

These compositions for topical or ocular application comprise at least one compound of formula (I), or one of its optical or geometric isomers or one of its salts, etc., in a concentration which preferably ranges from 0.001% to 5% by weight relative to the total weight of the composition.

The compounds of formula (I) according to the invention also find application in the cosmetic field, in particular for body and hair care and, especially, for the treatment of skins with a tendency to acne, for hair regrowth, for preventing hair loss, for combating the greasy appearance of the skin or hair, in the protection against the harmful effects of the sun or in the treatment of physiologically dry skin, and for preventing and/or combating photoinduced or chronological aging.

For cosmetic applications, the compounds according to the invention can, moreover, be advantageously used in combination with other compounds displaying retinoid-type activity, with the D vitamins or derivatives thereof, with corticosteroids, with free-radical scavengers, with $\alpha$-hydroxy or $\alpha$-keto acids or derivatives thereof, or with ion channel blockers, all of these various active agents being as defined above.

The present invention therefore also features cosmetic compositions comprising a carrier, vehicle or diluent which is cosmetically acceptable and suitable for topical application, at least one compound of formula (I) or one of its optical or geometric isomers or one of its salts. Such cosmetic compositions are advantageously presented, in particular, in the form of a cream, milk, lotion, gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total weight of the composition.

The medicinal and cosmetic compositions according to the invention may, in addition, contain inert or even pharmacodynamically or cosmetically active additives or adjuvants, or combinations of these additives/adjuvants and, in particular: wetting agents; depigmenting agents such as hydroquinone, azelaic acid, caffeic acid or kojic acid; emollients; moisturizers such as glycerol, PEG 400, thiamorpholinone and derivatives thereof, or urea; antiseborrhoeic or antiacne agents, such as S-carboxymethylcysteine, S-benzylcysteamine, salts thereof or derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents promoting hair regrowth, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,4-diphenylimidazolidine-2,4-dione); nonsteroidal anti-inflammatories; carotenoids, and especially $\beta$-carotene; antipsoriatic agents such as anthralin and derivatives thereof; and, lastly, 5,8,11,14-eicosa-tetraynoic and 5,8,11-eicosatriynoic acid and the esters and amides thereof.

The compositions according to the invention may also comprise taste—or flavor enhancers, preservatives such as esters of para-hydroxybenzoic acid, stabilizers, moisture-regulating agents, pH-regulating agents, agents which modify osmotic pressure, emulsifiers, UV-A and UV-B screening agents, and antioxidants, such as $\alpha$-tocopherol, butylhydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of 6-(5,6,7,8-tetrahydro-5,5,8,8-tetramethyl-2-naphthyloxy)naphthoic acid:

(a) Preparation of methyl 6-(5,6,7,8-tetrahydro-5,5,8,8-tetramethyl-2-naphthyloxy)naphthoate:

5.3 g (15 mmol) of 5,6,7,8-tetrahydro-5,5,8,8-tetramethyl-2-naphthol and 70 ml of pyridine were introduced into a three-necked flask under a stream of nitrogen, and then 430 mg (15 mmol) of sodium hydride (80% in oil) were added in small portions. The mixture was stirred for thirty minutes, 4 g (15 mmol) of methyl 6-bromo-2-naphthoate and 4.6 g (22.5 mmol) of a complex of copper bromide and dimethyl sulfide were added in succession, and the mixture was heated at reflux for sixteen hours. The reaction medium was evaporated to dryness, the residue was taken up in water and ethyl ether, and the organic phase was decanted, dried over magnesium sulfate and then evaporated. The residue obtained was purified by chromatography on a silica column eluted with dichloromethane. After evaporation of the solvents, 3.1 g (53%) of the expected methyl ester were recovered, having a melting point of 141°–4° C.

(b) Synthesis of 6-(5,6,7,8-tetrahydro-5,5,8,8-tetramethyl-2-naphthyloxy)naphthoic acid:

3.1 g (8 mmol) of the ester obtained in (a), 40 ml of THF and 40 ml of 2N methanolic sodium hydroxide solution were introduced into a round-bottomed flask and the mixture was stirred at room temperature for eight hours. The reaction medium was evaporated to dryness, the residue was taken up in water, the mixture was acidified to a pH of 1 and subjected

9 to extraction with ethyl ether, and the organic phase was decanted, dried over magnesium sulfate and evaporated. The residue obtained was purified by chromatography on a silica column eluted with a mixture of dichloromethane and ethyl ether (97:3). After evaporation of the solvents, 1.3 g (44%) of the expected acid was recovered, having a melting point of 231°–2° C.

EXAMPLE 2
Preparation of 4-(5,6,7,8-tetrahydro-5,5,8,8-tetramethyl-2-naphthyloxy)cinnamic acid:

(a) Preparation of 4-(5,6,7,8-tetrahydro-5,5,8,8-tetramethyl-2-naphthyloxy)benzaldehyde:

Utilizing a procedure analogous to that of Example 1(a), 5.3 g (15 mmol) of 5,6,7,8-tetra-hydro-5,5,8,8-tetramethyl-2-naphthol were reacted with 3.1 g (16.5 mmol) of 4-bromobenzaldehyde to provide, after purification by chromatography on a silica column eluted with a mixture of dichloromethane and hexane (50:50), 2.4 g of the expected aldehyde having a melting point of 75°–6° C.

(b) Preparation of ethyl 4-(5,6,7,8-tetrahydro-5,5,8,8-tetramethyl-2-naphthyloxy)cinnamate:

224 mg (8 mmol) of sodium hydride (80% in oil) and 50 ml of dimethoxyethane were introduced into a three-necked flask under a stream of nitrogen, and a solution of 1.6 ml (8 mmol) of triethyl phosphonium acetate in 10 ml of dimethoxy ethane was added dropwise. The mixture was stirred at room temperature for one hour, and a solution of 2.4 g (7.8 mmol) of the aldehyde obtained in (a) in 20 ml of dimethoxy ethane was added dropwise at 0° C. The mixture was stirred at room temperature for four hours, the reaction medium was poured into water and extracted with ethyl ether, and the organic phase was decanted, dried over magnesium sulfate and evaporated. The residue obtained was purified by chromatography on a silica column eluted with a mixture of dichloromethane and hexane (30:70), and 2.2 g (74%) of the expected ethyl ester were recovered.

(c) Synthesis of 4-(5,6,7,8-tetrahydro-5,5,8,8-tetramethyl-2-naphthyloxy)cinnamic acid:

Utilizing a procedure analogous to that of Example 1(b), from 2.2 g (5.8 mmol) of ethyl 4-(5,6,7,8-tetra-hydro-5,5,8,8-tetramethyl-2-naphthyloxy)cinnamate, 1.5 g (75%) of the expected acid was obtained, having a melting point of 220°–1° C.

EXAMPLE 3
Preparation of β-methyl-4-(5,6,7,8-tetrahydro-5,5,8,8-tetramethyl-2-naphthyloxy)cinnamic acid:

(a) Preparation of 4-(5,6,7,8-tetrahydro-5,5,8,8-tetramethyl-2-naphthyloxy)acetophenone:

Utilizing a procedure analogous to that of Example 1 (a), 6.6 g (32 mmol) of 5,6,7,8-tetrahydro-5,5,8,8-tetramethyl-2-naphthol were reacted with 5.4 g (27 mmol) of 4-bromoacetophenone to provide 6.3 g (72%) of the expected acetone, in the form of a pale yellow oil.

(b) Preparation of ethyl β-methyl-4-(5,6,7,8-tetrahydro-5,5,8,8-tetramethyl-2-naphthyloxy)cinnamate:

Utilizing a procedure analogous to that of Example 2(b), 3 g (9.3 mmol) of 4-(5,6,7,8-tetra-hydro-5,5,8,8-tetramethyl-2-naphthyloxy)acetophenone were reacted with 2.5 g (11.2 mmol) of triethyl phosphonoacetate to provide, after chromatography on a silica column eluted with a mixture of dichloromethane and hexane (30:70), 2.6 g (72%) of the ethyl ester in the form of a colorless oil.

(c) Synthesis of β-methyl-4-(5,6,7,8-tetrahydro-5,5,8,8-tetra-methyl-2-naphthyloxy)cinnamic acid:

Utilizing a procedure analogous to that of Example 1(b), from 2.6 g (6.6 mmol) of the ethyl ester obtained in (b), 1.1 g (46%) of the expected acid was obtained, having a melting point of 156°–7° C.

EXAMPLE 4
Preparation of 4-(5,6,7,8-tetrahydro-5,5,8,8-tetramethyl-2-naphthyloxy)phenylpropiolic acid:

(a) Preparation of 4-(5,6,7,8-tetrahydro-5,5,8,8-tetramethyl-2-naphthyloxy)Phenylacetylene:

0.87 ml (6.2 mmol) of diisopropylamine and 20 ml of THF were introduced into a three-necked flask under a stream of nitrogen. 2.5 ml (6.2 mmol) of n-butyllithium (2.5M in hexane) were added dropwise at −78° C. and the mixture was stirred at this temperature for 15 minutes. Subsequently, a solution of 2 g (6.2 mmol) of 4-(5,6,7,8-tetrahydro-5,5,8,8-tetramethyl-2-naphthyloxy) acetophenone, prepared in Example 3(a), in 10 ml of THF was added. After stirring at −78° C. for one hour, the solution was treated with 0.9 ml (6.2 mmol) of diethyl chlorophosphate and the temperature was permitted to return to room temperature.

This solution was transferred into a solution of lithium diisopropylamide (prepared using 1.74 ml (12.4 mmol) of diisopropylamine and 5 ml (12.4 mmol) of n-butyllithium (2.5M in hexane) in 30 ml of THF at −78° C. The temperature was permitted to return to room temperature and the mixture was stirred for twelve hours. The reaction medium was poured into ice-water and the pH was adjusted to 1 with 5N hydrochloric acid. The acidified medium was extracted with ethyl ether and the organic phase was decanted, dried over magnesium sulfate and evaporated. The residue obtained was purified by chromatography on a silica column eluted with hexane. After evaporation of the solvents, 0.83 g (44%) of the acetylene derivative was recovered, in the form of a colorless oil.

(b) Synthesis of 4-(5,6,7,8-tetrahydro-5,5,8,8-tetramethyl-2-naphthyloxy)phenylpropiolic acid:

0.82 g (2.7 mmol) of the acetylene compound obtained in (a) and 10 ml of THF were introduced into a three-necked flask under a stream of nitrogen. 1.85 ml (2.9 mmol) of n-butyllithium (1.6M in hexane) was added dropwise at −78° C. and the mixture was stirred for thirty minutes. A stream of $CO_2$ was charged therein for fifteen minutes at −78° C. and the temperature was permitted to return to room temperature. The reaction medium was poured into aqueous ammonium chloride solution and extracted with ethyl ether, and the organic phase was decanted, dried over magnesium sulfate and evaporated. The residue obtained was purified by chromatography on a silica column eluted with dichloromethane. After evaporation of the solvents, 490 mg (53%) of the expected acid were recovered, having a melting point of 166°–8° C.

EXAMPLE 5
Preparation of 6-(3,5,5,8,8-pentamethyl-5,6,7,8-tetrahydro-2-naphthyloxy)naphthoic acid:

(a) Preparation of 3,5,5,8,8-Pentamethyl-5,6,7,8-tetrahydro-2-naphthol:

50.8 g (0.27 mol) of 2,5-dichloro-2,5-dimethylhexane, 30 g (0.27 mol) of 2-methylphenol and 500 ml of dichloromethane were introduced into a three-necked flask. 14.8 g (0.11 mol) of aluminum chloride were added in small portions at 0° C., and the mixture was stirred at room temperature for twelve hours. The reaction medium was poured into ice-water and extracted with dichloromethane, and the organic phase was decanted, washed with aqueous bicarbonate, dried over magnesium sulphate and evaporated. The residue obtained was triturated in hexane, the mixture was filtered, and, after drying, 54.4 g (90%) of the expected phenol were recovered, having a melting point of 125°–6° C.

(b) Preparation of methyl 6-(3,5,5,8,8-pentamethyl-5,6,7,8-tetra-hydro-2-naphthyloxy)naphthoate:

Utilizing a procedure analogous to that of Example 1(a), 1.1 g (5 mmol) of 3,5,5,8,8-penta-methyl-5,6,7,8-tetrahydro-2-naphthol was reacted with 1.1 g (4.1 mmol) of methyl 6-bromonaphthoate to provide 1.1 g (70%) of the expected methyl ester.

(c) Synthesis of 6-(3,5,5,8,8-pentamethyl-5,6,7,8-tetrahydro-2-naphthyloxy)naphthoic acid:

Utilizing a procedure analogous to that of Example 1(b), from 1.1 g (2.9 mmol) of the methyl ester obtained in (b), 600 mg (53%) of the expected acid were obtained, having a melting point of 237°–9° C.

EXAMPLE 6

Preparation of 6-(5,6,7,8-Tetrahydro-5,5,8,8-tetramethyl-2-naphthylthio)naphthoic acid:

(a) Preparation of butyl 6-(5,6,7,8-tetrahydro-5,5,8,8-tetramethyl-2-naphthylthio)naphthoate:

30 ml of n-butyl alcohol were introduced into a round-bottomed flask, 500 mg (23 mmol) of sodium were added in small portions, and the mixture was stirred for thirty minutes. Subsequently, 2 g (9.1 mmol) of 5,6,7,8-tetra-hydro-5,5,8,8-tetramethyl-2-naphthylthiol, 2.4 g (9.1 mmol) of methyl 6-bromo-2-naphthoate and 420 mg (0.36 mmol) of tetrakis(triphenylphosphine)palladium(0) were added in succession, and the mixture was then heated at reflux for four hours. The reaction medium was evaporated, the residue was taken up in water and ethyl acetate, and the organic phase was decanted, washed with water, dried over magnesium sulfate and evaporated. The residue obtained was purified by chromatography on a silica column eluted with dichloromethane. After evaporation of the solvents, 2.2 g (55%) of the butyl ester were recovered.

(b) Synthesis of 6-(5,6,7,8-tetrahydro-5,5,8,8-tetramethyl-2-naphthylthio)naphthoic acid:

Utilizing a procedure analogous to that of Example 1(b), from 2.1 g (4.8 mmol) of the butyl ester obtained in (a), 1.7 g (90%) of the expected acid was obtained, having a melting point of 194°–5° C.

EXAMPLE 7

Preparation of 6-(5,6,7,8-tetrahydro-5,5,8,8-tetramethyl-2-naphthylsulfinyl)naphthoic acid:

(a) Preparation of butyl 6-(5,6,7,8-tetrahydro-5,5,8,8-tetramethyl-2-naphthylsulfinyl)naphthoate:

1.6 g (3.5 mmol) of butyl 6-(5,6,7,8-tetra-hydro-5,5,8,8-tetramethyl-2-naphthylthio)naphthoate and 30 ml of dichloromethane were introduced into a round-bottomed flask, and 1.1 g (3.5 mmol) or meta-chloroper-benzoic acid was added. The mixture was stirred at room temperature for two hours, the reaction medium was poured into water and extracted with dichloromethane, and the organic phase was decanted, dried over magnesium sulfate and evaporated. The residue was purified by chromatography on a silica column eluted with dichloromethane. After evaporation of the solvents, 1.3 g (78%) of the expected ester was recovered.

(b) Synthesis of 6-(5,6,7,8-tetrahydro-5,5,8,8-tetramethyl-2-naphthylsulfinyl)naphthoate acid:

Utilizing a procedure analogous to that of Example 1(b), from 1.2 g (2.6 mmol) of the butyl ester obtained in (a), 850 mg (81w) of the expected acid were obtained, having a melting point of 183°–5° C.

EXAMPLE 8

Preparation of 6-(5,6,7,8-tetrahydro-5,5,8,8-tetramethyl-2-naphthylsulfonyl)naphthoic acid:

(a) Preparation of butyl 6-(5,6,7,8-tetrahydro-5, 5,8, 8-tetramethyl-2-naphthylsulfonyl)naphthoate:

2.2 g (5.1 mmol) of butyl 6-(5,6,7,8-tetra-hydro-5,5,8,8-tetramethyl-2-naphthylthio)naphthoate and 30 ml of dichloromethane were introduced into a round-bottomed flask, and 4.3 g (12.6 mmol) of meta-chloroperbenzoic acid were added. The mixture was stirred at room temperature for two hours, the reaction medium was poured into water and extracted with dichloromethane, and the organic phase was decanted, dried over magnesium sulfate and evaporated. The residue was purified by chromatography on a silica column eluted with dichloromethane. After evaporation of the solvents, 1.74 g (72w) of the expected ester was recovered.

(b) Synthesis of 6-(5,6,7,8-tetrahydro-5,5,8,8-tetramethyl-2-naphthylsulfonyl)naphthoic acid:

Utilizing a procedure analogous to that of Example 1(b), from 1.74 g (3.6 mmol) of the butyl ester obtained in (a), 1.54 g (99w) of the expected acid Was obtained, having a melting point of 256°–8° C.

EXAMPLE 9

Preparation of 6-(5,6,7,8-tetrahydro-5,5,8,8-tetramethyl-2-naphthylamino)naphthoic acid:

(a) Preparation of methyl 6-(5,6,7,8-tetrahydro-5,5,8,8-tetramethyl-2-naphthylamino)naphthoate:

4.04 g (19.9 mmol) of 5,6,7,8-tetrahydro-5,5,8,8-tetramethyl-2-naphthylamine, 5 g (19.9 mmol) of 6-bromo-2-naphthoic acid, 3.3 ml (30 mmol) of N-methylmorpholine, 2.9 g (19.9 mmol) of $Cu_2O$ and 60 ml of dioxane were introduced in succession into a round-bottomed flask. The mixture was heated at reflux for 24 hours, the reaction medium was poured into 60 ml of 5N hydrochloric acid, and the precipitate was filtered off, washed with water and dried. The solid was purified by chromatography on a silica column eluted with ethyl acetate and, after evaporation of the solvents, 1.2 g of the expected acid was recovered, which was converted into the methyl ester by reacting same with 50 ml of methyl alcohol in the presence of 100 µl of concentrated sulfuric acid. 720 mg (10%) of methyl 6-(5,6,7,8-tetrahydro-5,5,8,8-tetramethyl-2-naphthylamino)-naphthoate were obtained, in the form of a chestnut-brown oil.

(b) Synthesis of 6-(5,6,7,8-tetrahydro-5,5,8,8-tetramethyl-2-naphthylamino)naphthoic acid:

Utilizing a procedure analogous to that of Example 1(b), from 700 mg (1.8 mmol) of the methyl ester obtained in (a), 670 mg (99%) of the expected acid were obtained, having a melting point of 246°–8° C.

EXAMPLE 10

Preparation of a-acetamido-4-(5,6,7,8-tetrahydro-5,5,8,8-tetra-methyl-2-naphthyloxy)cinnamic acid:

(a) Preparation of 2-methyl-4-[4-(5,6,7,8-tetrahydro-5,5, 8,8-tetra-methyl-2-naphthyloxy)benzylidene]oxazol-5-one:

8.3 g (27 mmol) of 4-(5,6,7,8-tetrahydro-5,5, 8,8-tetramethyl-2-naphthyloxy)benzaldehyde, 3.8 g (32 mmol) of N-acetylglycine, 2.9 g (35 mmol) of sodium acetate and 13.8 g (135 mmol) of acetic anhydride were introduced into a round-bottomed flask. The mixture was heated at 120° C. for eight hours, the reaction medium was poured into water, and the precipitate was filtered and washed with a solution of ethyl alcohol and water (50:50). After purification by chromatography on a silica column eluted with a mixture of dichloromethane and hexane (60:40), 8.9 g (85%) of the expected compound were recovered, having a melting point of 145°–7° C.

(b) Synthesis of a-acetamido-4-(5,6,7,8-tetrahydro-5,5,8, 8-tetra-methyl-2-naphthyloxy)cinnamic acid:

3.6 g (9 mmol) of the compound obtained in (a), 38 mg (0.4 mmol) of sodium acetate and 100 ml of a mixture of water and acetone (80:20) were introduced into a round-bottomed flask. The mixture was heated at reflux for sixteen hours, the reaction medium was cooled to room temperature, and the solid was filtered off, washed with water and dried at 60° C. 3.5 g (92%) of the expected acid were recovered, having a melting point of 194°–6° C.

EXAMPLE 11

Preparation of α-hydroxy-4-(5,6,7,8-tetrahydro-5,5,8,8-tetra-methyl-2-naphthyloxy)cinnamic acid:

1.6 g of (4 mmol) of α-acetamido-4-(5,6,7,8-tetrahydro-5,5,8,8-tetramethyl-2-naphthyloxy)cinnamic acid, 25 ml of concentrated hydrochloric acid and 25 ml of ethyl alcohol were introduced into a round-bottomed flask and the mixture was heated at reflux for eight hours. The reaction medium was poured into water and extracted with ethyl acetate, and the organic phase was decanted, washed with water, dried over magnesium sulfate and evaporated. The residue obtained was triturated in a mixture of hexane and ethyl ether (80:20) and the mixture was filtered. 1.06 g (72%) of the expected acid was recovered, having a melting point of 207°–10° C.

EXAMPLE 12

Preparation of 6-(3,5,5,8,8-pentamethyl-5,6,7,8-tetrahydro-2-naphthylthio)naphthoic acid:

(a) Preparation of 0-3,5,5,8,8-pentamethy-5,6,7,8-tetrahydro-2-naphthyl dimethylthiocarbamate:

4.1 g (0.138 mol) of sodium hydride (80% in oil) and 200 ml of DMF were introduced into a round-bottomed flask under a stream of nitrogen. The mixture was cooled to 0° C. and a solution of 25.2 g (0.115 mol) of 3,5,5,8,8-pentamethyl-5,6,7,8-tetrahydro-2-naphthol in 100 ml of DMF was added dropwise, and the mixture was stirred until the evolution of gas ceased; subsequently, a solution of 18.55 g (0.15 mol) of dimethylthiocarbamoyl chloride in 200 ml of DMF was added and the mixture was stirred at room temperature for eight hours. The reaction medium was poured into water and extracted with ethyl acetate, and the organic phase was decanted, washed with water, dried over magnesium sulfate and evaporated. The solid obtained was purified by chromatography on a silica column eluted with a mixture of ethyl acetate and hexane (30:70). After evaporation of the solvents, 20 g (68%) of the expected compound were recovered, having a melting point of 110°–1° C.

(b) Preparation of S-3,5,5,8,8-pentamethyl-5,6,7,8-tetrahydro-2-naphthyl dimethylthiocarbamate:

20.1 g (65.8 mmol) of the compound obtained in (a) were introduced into a round-bottomed flask under a stream of nitrogen and were heated at 240° C. for six hours. The reaction medium was extracted with dichloromethane, the extract was washed with water, and the organic phase was decanted, dried over magnesium sulfate and evaporated. 18.1 g (90%) of the expected compound were recovered, having a melting point of 138°–9° C.

(c) Preparation of 3,5,5,8,8-Pentamethyl-5,6,7,8-tetrahydro-2-naphthylthiol:

23 g (75 mmol) of the compound obtained in (b) and 300 ml of methyl alcohol were introduced into a round-bottomed flask. 30 g (75 mmol) of sodium hydroxide were added and the mixture was heated at reflux for three hours. The reaction medium was evaporated, the residue was taken up in water, and the mixture was acidified with concentrated hydrochloric acid and filtered. The solid obtained was washed with water and dried, and 18 g (99%) of 3,5,5,8,8-pentamethyl-5,6,7,8-tetrahydro-2-naphthylthiol were recovered, having a melting point of 97°–8° C.

(d) Preparation of butyl 6-(3,5,5,8,8-pentamethyl-5,6,7,8-tetra-hydro-2-naphthylthio)naphthoate:

Utilizing a procedure analogous to that of Example 6(a), 4 g (17 mmol) of 3,5,5,8,8-pentamethyl-5,6,7,8-tetrahydro-2-naphthylthiol were reacted with 4.5 g (17 mmol) of methyl 6-bromo-2-naphthoate to provide, after chromatography on a silica column eluted with dichloromethane, 5 g (64%) of the butyl ester.

(e) Synthesis of 6-(3,5,5,8,8-pentamethyl-5,6,7,8-tetrahydro-2-naphthylthio)naphthoic acid:

Utilizing a procedure analogous to that of Example 1(b), from 2 g (4.3 mmol) of the butyl ester obtained in (d), 1.22 g (70%) of the expected acid was obtained, having a melting point of 257°–8° C.

EXAMPLE 13

Preparation of 6-(3,5,5,8,8-pentamethyl-5,6,7,8-tetrahydro-2-naphthylsulfonyl)naphthoic acid:

(a) Preparation of butyl 6-(3,5,5,8,8-pentamethyl-5,6,7,8-tetrahydro-2-naphthylsulfonyl)naphthoate:

Utilizing a procedure analogous to that of Example 8(a), from 2.7 g (5.8 mmol) of butyl 4-(3,5,5,8,8-pentamethyl-5,6,7,8-tetrahydro-2-naphthylthio)naphthoate and after purification by chromatography on a silica column eluted with dichloromethane, 2.3 g (80%) of the expected butyl ester were obtained.

(b) Synthesis of 6-(3,5,5,8,8-pentamethyl-5,6,7,8-tetrahydro-2-naphthylsulfonyl)naphthoic acid:

Utilizing a procedure analogous to that of Example 1(b), from 2.3 g (4.6 mmol) of the butyl ester obtained in (a), 1.32 g (65%) of the expected acid was obtained, having a melting point of 274°–6° C.

EXAMPLE 14

Preparation of 6-(3-bromo-5,6,7,8-tetrahydro-5,5,8,8-tetramethyl-2-naphthyloxy)naphthoic acid:

(a) Preparation of 4-bromo-5,6,7,8-tetrahydro-5,5,8,8-tetramethyl-2-naphthol:

Utilizing a procedure analogous to that of Example 5(a), 3 g (16.4 mmol) of 2,5-dichloro-2,5-dimethylhexane were reacted with 15 ml (16.4 mmol) of 2-bromophenol to provide, after purification by chromatography on a silica column eluted with a mixture of ethyl acetate and heptane (10:90), 2.7 g (58%) of the expected phenol.

(b) Preparation of methyl 6-(3-bromo-5,6,7,8-tetrahydro-5,5,8,8-tetramethyl-2-naphthyloxy)naphthoate:

Utilizing a procedure analogous to that of Example 1(a), 1 g (3.5 mmol) of 3-bromo-5,6,7,8-tetrahydro-5,5,8,8-tetramethyl-2-naphthol was reacted with 0.78 g (2.9 mmol) of methyl 6-bromo-2-naphthoate to provide 460 mg (33%) of the expected methyl ester, having a melting point of 145°–6° C.

(c) Synthesis of 6-(3-bromo-5,6,7,8-tetrahydro-5,5,8,8-tetra-methyl-2-naphthyloxy)naphthoic acid:

Utilizing a procedure analogous to that of Example 1(b), from 700 mg (1.7 mmol) of the methyl ester obtained in (b), 650 mg (95%) of the expected acid were obtained, having a melting point of 229°–30° C.

EXAMPLE 15

Preparation of 6-(5,6,7,8-tetrahydro-5,5,8,8-tetramethyl-2-naphthyloxy)naphthalenemethanol:

2 g (5.1 mmol) of methyl 6-(5,6,7,8-tetra-hydro-5,5,8,8-tetramethyl-2-naphthyloxy)naphthoate (prepared in Example 1(a)) and 60 ml of THF were introduced into a three-necked flask. 300 mg (7.7 mmol) of lithium aluminum hydride were introduced under a stream of nitrogen, and the mixture was stirred at room temperature for two hours. Sodium sulfate hydrate was added, and the mixture was stirred until the excess hydride had hydrolysed. The salt was filtered off and the filtrate was evaporated. 1.91 g (99%) of the expected alcohol was recovered, having a melting point of 131°–3° C.

EXAMPLE 16
Preparation of N-ethyl-6-(5,6,7,8-tetrahydro-5,5,8,8-tetramethyl-2-naphthyloxy)naphthalenecarboxamide:

(a) Preparation of 6-(5,6,7,8-tetrahydro-5,5,8,8-tetramethyl-2-naphthyloxy)naphthoyl chloride:

1 g (2.6 mmol) of 6-(5,6,7,8-tetrahydro-5,5,8,8-tetramethyl-2-naphthyloxy)naphthoic acid (prepared in Example 1(b)), 10 ml of toluene and 50 µl of DMF wee introduced into a round-bottomed flask. 230 µl (3.2 mmol) of thionyl chloride were added and the mixture was heated at 80° C. for one hour. The reaction medium was evaporated to dryness and the crude acid chloride was recovered, for use as is, in the subsequent synthesis.

(b) Synthesis of N-ethyl-6-(5,6,7,8-tetrahydro-5,5,8,8-tetramethyl-2-naphthyloxy)naphthalene carboxamide:

520 µl (6.4 mmol) of ethylamine (70% in water) and 5 ml of THF were introduced into a round-bottomed flask. A solution of 1.05 g (2.6 mmol) of the acid chloride obtained in (a) in 5 ml of THF was added dropwise and the mixture was stirred at room temperature for one hour. The reaction medium was poured into water and extracted with ethyl acetate, and the organic phase was decanted, dried over magnesium sulfate and evaporated. 1 g (93%) of the expected amide was recovered, with a melting point of 168°–70° C.

EXAMPLE 17
Preparation of 6-(5,6,7,8-tetrahydro-5,5,8,8-tetramethyl-2-naphthyloxy)naphthalene carboxamide:

Utilizing a procedure analogous to that of Example 16(b), 671 mg (1.7 mmol) of 6-(5,6,7,8-tetrahydro-5,5,8,8-tetramethyl-2-naphthyloxy)naphthoyl chloride were reacted with 10 ml of aqueous ammonia (32%) to provide 560 mg (88%) of the expected amide, having a melting point of 175°–6° C.

EXAMPLE 18
Preparation of 6-(5,6,7,8-tetrahydro-5,5,8,8-tetramethyl-2-naphthyloxy)naphthoic acid morpholide:

Utilizing a procedure analogous to that of Example 16(b), 593 mg (1.5 mmol) of 6-(5,6,7,8-tetrahydro-5,5,8,8-tetramethyl-2-naphthyloxy)naphthoyl chloride were reacted with 320 µl (3.6 mmol) of morpholine to provide 470 mg (70%) of the expected amide, having a melting point of 118°–20° C.

EXAMPLE 19
Preparation of 6-(5,6,7,8-tetrahydro-5,5,8,8-tetramethyl-2-naphthyloxy)naphthalene carbaldehyde:

100 ml of dichloromethane and 1.7 g (4.5 mmol) of pyridinium dichromate were introduced into a round-bottomed flask. The mixture was cooled to 0° C. and a solution of 1.2 g (3.3 mmol) of 6-(5,6,7,8-tetra-hydro-5,5,8,8-tetramethyl-2-naphthyloxy)naphthalene methanol in 20 ml of dichloromethane was added dropwise. The mixture was stirred at room temperature for one hour, the reaction medium was filtered over silica, the filtrate was evaporated to dryness and the solid was triturated in heptane and filtered off. 1.07 g (90%) of the expected aldehyde was recovered, having a melting point of 123°–4° C.

EXAMPLE 20
In this example, various specific formulations based on the compounds according to the invention are illustrated.

(A) FOR ORAL ADMINISTRATION:

(a) 0.2 g Tablet:

| | | |
|---|---|---|
| (i) | Compound of Example 1 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vii) | Magnesium stearate | 0.005 g |

(b) Oral suspension in 5 ml ampoules:

| | | |
|---|---|---|
| (i) | Compound of Example 2 | 0.001 g |
| (ii) | Glycerin | 0.500 g |
| (iii) | Sorbitol at 70% | 0.500 g |
| (iv) | Sodium saccharinate | 0.010 g |
| (v) | Methyl para-hydroxybenzoate | 0.040 g |
| (vi) | Flavoring | qs |
| (vii) | Purified water | qs 5 ml |

(c) 0.8 g Tablet:

| | | |
|---|---|---|
| (i) | Compound of Example 6 | 0.500 g |
| (ii) | Pregelatinated starch | 0.100 g |
| (iii) | Microcrystalline cellulose | 0.115 g |
| (iv) | Lactose | 0.075 g |
| (v) | Magnesium stearate | 0.010 g |

(d) Oral suspension in 10 ml ampoules:

| | | |
|---|---|---|
| (i) | Compound of Example 4 | 0.05 g |
| (ii) | Glycerin | 1.000 g |
| (iii) | Sorbitol at 70% | 1.000 g |
| (iv) | Sodium saccharinate | 0.010 g |
| (v) | Methyl para-hydroxybenzoate | 0.080 g |
| (vi) | Flavoring | qs |
| (vii) | Purified water | qs 10 ml |

(B) FOR TOPICAL APPLICATION:

(a) Ointment:

| | | |
|---|---|---|
| (i) | Compound of Example 1 | 0.020 g |
| (ii) | Isopropyl myristate | 81.700 g |
| (iii) | Liquid petroleum | 9.100 g |
| (iv) | Silica ("Aérosil 200" marketed by DEGUSSA) | 9.180 g |

(b) Ointment:

| | | |
|---|---|---|
| (i) | Compound of Example 6 | 0.300 g |
| (ii) | White vaseline, codex | 100 g |

(c) Nonionic water-in-oil cream:

| | | |
|---|---|---|
| (i) | Compound of Example 1 | 0.100 g |
| (ii) | Mixture of emulsive lanolin alcohols, waxes and oils ("Eucerine anhydre" marketed by BDF) | 39.900 g |
| (iii) | Methyl para-hydroxybenzoate | 0.075 g |
| (iv) | Propyl para-hydroxybenzoate | 0.075 g |
| (v) | Sterile demineralized water | qs 100 g |

(d) Lotion:

| | | |
|---|---|---|
| (i) | Compound of Example 1 | 0.100 g |
| (ii) | Polyethylene glycol (PEG 400) | 69.900 g |
| (iii) | Ethanol at 95% | 30.000 g |

(e) Hydrophobic ointment:

| | | |
|---|---|---|
| (i) | Compound of Example 2 | 0.300 g |
| (ii) | Isopropyl myristate | 36.400 g |
| (iii) | Silicone oil ("Rhodorsil 47 V 300" marketed by RHÔNE-POULENC) | 36.400 g |
| (iv) | Beeswax | 13.600 g |
| (v) | Silicone oil ("Abil 300.000 cst" marketed by GOLDSCHMIDT) | 100 g |

(f) Nonionic oil-in-water cream:

| | | |
|---|---|---|
| (i) | Compound of Example 4 | 0.500 g |
| (ii) | Cetyl alcohol | 4.000 g |
| (iii) | Glycerol monostearate | 2.500 g |

| (iv) | PEG 50 stearate | 2.500 g |
| (v) | Shea butter | 9.200 g |
| (vi) | Propylene glycol | 2.000 g |
| (vii) | Methyl para-hydroxybenzoate | 0.075 g |
| (viii) | Propyl para-hydroxybenzoate | 0.075 g |
| (ix) | Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A bicyclic aromatic compound having the structural formula (I):

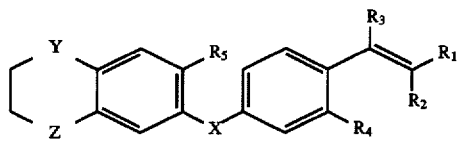

in which $R_1$, is a radical —CO—$R_{10}$, $R_3$ is a hydrogen atom or a lower alkyl radical, $R_2$ and $R_4$ together form, with the benzene ring from which they depend, a naphthalene ring member, in which $R_7$ is as defined below; $R_5$ is a hydrogen atom, a halogen atom, a lower alkyl radical, an $NO_2$ radical, a hydroxyl radical, a radical —$OR_7$, or a radical:

in which $R_7$, $R_{13}$ and $R_{14}$ are as defined below; X is —O—, or —S(O)$_t$—, wherein t is as defined below; Y and Z, which may be identical or different, are each —$CR_{13}R_{14}$—, —O— or —S(O)$_t$—, with the proviso that Y and Z cannot simultaneously be an oxygen atom and cannot simultaneously be a radical —S(O)$_t$—, wherein t, $R_{13}$ and $R_{14}$ are as defined below; $R_7$ is a lower alkyl radical; $R_{10}$ is

a radical —O—$R_{11}$, wherein $R_{11}$ is a hydrogen atom, a linear or branched alkyl radical having from 1 to 20 carbon atoms, an alkenyl radical, a mono- or polyhydroxyalkyl radical, an optionally substituted aryl or aralkyl radical, a sugar radical, or an amino acid residue or peptide residue; $R_{13}$, and $R_{14}$ are each a hydrogen atom, or a lower alkyl radical; t is 0, 1 or 2; or a pharmaceutically/cosmetically acceptable salt or optical or geometric isomer thereof.

2. A bicyclic aromatic compound as defined by claim 1, comprising a pharmaceutically acceptable salt thereof.

3. A bicyclic aromatic compound as defined by claim 1, wherein formula (I), the lower alkyl radical substituents are selected from among methyl, ethyl, isopropyl, butyl, tert-butyl, hexyl, nonyl and dodecyl radicals.

4. A bicyclic aromatic compound as defined by claim 1, wherein formula (I), the linear or branched alkyl radical substituents having from 1 to 20 carbon atoms are selected from among methyl, ethyl, propyl, 2-ethylhexyl, octyl, dodecyl, hexadecyl and octadecyl radicals.

5. A bicyclic aromatic compound as defined by claim 1, wherein formula (I), the monohydroxyalkyl radical substituents are selected from among 2-hydroxyethyl, 2-hydroxypropyl and 3-hydroxypropyl radicals.

6. A bicyclic aromatic compound as defined by claim 1, wherein formula (I), the aryl radical substituents are selected from among phenyl radicals optionally substituted by at least one halogen atom, or at least one hydroxyl or nitro functional group.

7. A bicyclic aromatic compound as defined by claim 1, wherein formula (I), the aralkyl radical substituents are selected from among benzyl and phenethyl radicals optionally substituted by at least one halogen atom, or at least one hydroxyl or nitro functional group.

8. A bicyclic aromatic compound as defined by claim 1, wherein formula (I), the alkenyl radical substituents have from 2 to 5 carbon atoms and comprise at least one site of ethylenic unsaturation.

9. A bicyclic aromatic compound as defined by claim 1, wherein formula (I), the halogen atom substituents are selected from among fluorine, chlorine and bromine atoms.

10. A bicyclic aromatic compound as defined by claim 1, selected from among 6-(5,6,7,8-tetrahydro-5,5,8,8-tetramethyl-2-naphthyloxy)naphthoic acid; 6- (3,5,5,8,8-pentamethyl-5,6,7,8-tetrahydro-2-naphthyloxy)naphthoic acid; 6-(3,5,5,8,8-pentamethyl-5,6,7,8-tetrahydro-2-naphthylthio)naphthoic acid; 6-(3,5,5,8,8-pentamethyl-5,6,7,8-tetrahydro-2-naphthylulfonyl)naphoic acid; and 6-(3-bromo-5,6,7,8-tetrahydro-5,5,8,8-tetramethyl-2-naphthyloxy)naphthoic acid.

11. A bicyclic aromatic compound as defined by claim 1, wherein formula (I) at least one of the following characteristics is/are satisfied:

$R_1$ is a radical —CO—$R_{10}$;

x represents —O—, or —S—;

$R_2$ represents a hydrogen atom or a lower alkyl radical; and $R_2$ and $R_4$ together form, with the benzene ring adjacent thereto, a naphthalene ring member.

12. A pharmaceutical composition of matter, comprising a therapeutically effective amount of a bicyclic aromatic compound as defined by claim 1, or pharmaceutically acceptable salt or isomer thereof, and a pharmaceutically acceptable vehicle, carrier or diluent therefor.

13. The pharmaceutical composition as defined by claim 12, further comprising a retinoid compound, a D vitamin or derivative thereof, a corticosteroid, an anti-free radical agent, an α-hydroxy or α-keto acid or derivative thereof, an ion channel blocker, or combination thereof.

14. A method for treating alopecia in a mammalian organism in need of such treatment, comprising administering to such organism a therapeutically effective amount of the pharmaceutical composition as defined by claim 12.

15. A method for treating a cardiovascular disorder in a mammalian organism in need of such treatment, comprising administering to such organism a therapeutically effective amount of the pharmaceutical composition as defined by claim 12.

16. A method for treating a dermatological, rheumatic, respiratory, cardiovascular or ophthalmologic disorder in a mammalian organism in need of such treatment, comprising administering to such organism a therapeutically effective amount of the pharmaceutical composition as defined by claim 12.

17. The method as defined by claim 16, comprising administering to such organism a daily dose of said bicyclic aromatic compound of about 0.01 mg/kg to 100 mg/kg of body weight thereof.

18. A cosmetic composition of matter, comprising a cosmetically effective amount of a bicyclic aromatic compound as defined by claim 1, or cosmetically acceptable salt or isomer thereof, and a cosmetically acceptable vehicle, carrier or diluent therefor.

19. The cosmetic composition as defined by claim 18, comprising a cream, a milk, a lotion, a gel, microspheres, nanospheres, lipid vesicles, polymeric vesicles, a soap, or a shampoo.

20. The cosmetic composition as defined by claim 18, comprising from 0.001% to 3% by weight of said bicyclic aromatic compound, or salt or isomer thereof.

21. The cosmetic composition as defined by claim 18, further comprising a retinoid compound, a D vitamin or derivative thereof, a corticosteroid, an anti-free radical agent, an α-hydroxy or α-keto acid or derivative thereof, an ion channel blocker, or combination thereof.

22. The pharmaceutical composition as defined by claim 12, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

23. The pharmaceutical composition as defined by claim 12, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

24. The cosmetic composition by claim 18, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

25. The cosmetic composition as defined by claim 18, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *